United States Patent [19]

Elsheikh

[11] Patent Number: 5,449,842
[45] Date of Patent: Sep. 12, 1995

[54] GAS PHASE PROCESS FOR THE PRODUCTION OF 1,1-DICHLORO-1-FLUOROETHANE AND/OR 1-CHLORO-1,1-DIFLUOROETHANE FROM VINYLIDENE CHLORIDE

[75] Inventor: Maher Y. Elsheikh, Tredyffrin, Pa.

[73] Assignee: Atochem North America, Inc., Philadelphia, Pa.

[21] Appl. No.: 110,472

[22] Filed: Aug. 23, 1993

Related U.S. Application Data

[63] Continuation of Ser. No. 864,145, Apr. 6, 1992, abandoned, which is a continuation of Ser. No. 591,588, Oct. 2, 1990, abandoned, which is a continuation-in-part of Ser. No. 333,475, Apr. 5, 1989, abandoned.

[51] Int. Cl.⁶ .............................................. C07C 17/08
[52] U.S. Cl. .................................. 570/765; 570/166; 570/167; 570/168
[58] Field of Search ................ 570/165, 166, 167, 168

[56] References Cited

U.S. PATENT DOCUMENTS

| | | |
|---|---|---|
| 2,637,747 | 5/1953 | McBee . |
| 3,755,477 | 8/1973 | Firth et al. . |
| 3,803,241 | 8/1974 | Stolkin et al. . |
| 3,836,479 | 9/1974 | Paucksch et al. . |
| 3,904,701 | 9/1975 | Schultz et al. . |
| 4,147,733 | 4/1979 | Fiske et al. . |
| 4,258,225 | 3/1981 | Feiring . |
| 4,374,289 | 2/1983 | Van Der Puy et al. . |
| 4,766,259 | 8/1988 | Manzer et al. . |
| 5,051,538 | 9/1991 | Gumprecht . |

FOREIGN PATENT DOCUMENTS

| | | | |
|---|---|---|---|
| 47208 | 12/1989 | Australia . | |
| 2388785 | 12/1978 | France | 570/167 |
| 1246703 | 8/1967 | Germany . | |
| 2739478 | 3/1978 | Germany | 570/186 |
| 2719021 | 11/1978 | Germany | 570/167 |
| 53-116305 | 10/1978 | Japan . | |
| 1309361 | 3/1973 | United Kingdom . | |
| 1556131 | 11/1979 | United Kingdom . | |
| 1585938 | 3/1981 | United Kingdom . | |

OTHER PUBLICATIONS

Feiring, J. Fluorine Chem. 14, 7–18 (1979).
Henne et al., J. Am. Chem. Soc. 65, 1271 (1943).
Henne et al., J. Am. Chem. Soc. 70:758 (1945).
McBee et al. Ind. Eng. Chem. 39 409–12 (1947).

Primary Examiner—Alan Siegel
Attorney, Agent, or Firm—Seidel Gonda Lavorgna & Monaco

[57] ABSTRACT

A novel gas phase process for the production of 1,1-dichloro-1-fluoroethane from vinylidene chloride and hydrogen fluoride is provided. The process is characterized by high conversion of vinylidene chloride to product, with a high selectivity for 1,1-dichloro-1-fluoroethane. The process may also be operated to selectively form 1-chloro-1,1-difluoroethane. Few volatile by-products and substantially no tar or oligomeric material is formed. Catalyst performance remains constant over extended periods of time.

39 Claims, No Drawings

GAS PHASE PROCESS FOR THE PRODUCTION OF 1,1-DICHLORO-1-FLUOROETHANE AND/OR 1-CHLORO-1,1-DIFLUOROETHANE FROM VINYLIDENE CHLORIDE

This is a continuation of co-pending application Ser. No. 07/864,145, filed on Apr. 6, 1992, now abandoned which is a continuation of application Ser. No. 07/591,588, filed on Oct.2, 1990, now abandoned, which is a continuation-in-part of co-pending application Ser. No. 333,475, filed Apr. 5, 1989, now abandoned.

FIELD OF THE INVENTION

The present invention relates to the manufacture of 1,1-dichloro-1-fluoroethane and/or 1-chloro-1,1-difluoroethane by fluorination of vinylidene chloride. Most particularly, it relates to a gaseous phase process for the fluorination of vinylidene chloride with hydrogen fluoride to selectively produce 1,1-dichloro-1-fluoroethane and/or 1-chloro-1,1-difluoroethane.

BACKGROUND OF THE INVENTION 1,1-Dichloro-1-fluoroethane is presently under consideration as a replacement for trichlorofluoromethane as a foam blowing agent. It has a substantially lower ozone depletion index than trichlorofluoromethane. Moreover, 1,1-dichloro-1-fluoroethane displays a 10–15% greater blowing efficiency in rigid foam, and improved solubility in aromatic polyester polyol, in comparison to trichlorofluoromethane. However, there is as yet no acceptable method for the efficient production of 1,1-dichloro-1-fluoroethane which is suitable for large scale commercial exploitation.

The liquid phase reaction of hydrogen fluoride and vinylidene chloride was reported by Henne and Plueddeman, J. Amer. Chem. Soc. 65, 1271 (1943). A mixture of hydrogen fluoride and vinylidene chloride was heated in a 4:1 molar ratio in an autoclave at 65° for 3 hours to give 50% 1,1-dichloro-1-fluoroethane, traces of 1-chloro-1,1-difluoroethane 10% of unreactive vinylidene chloride, 5% of 1,1,1-trichloroethane and 15% tar.

Henne and Arnold, J. Am. Chem. Soc. 70:758 (1945) describe the $BF_3$-catalyzed addition of hydrogen fluoride to various chlorofluoroolefins in the liquid phase at a molar ratio of HF to olefin of 2:1 at 95° C. However, the process is characterized by very low vinylidene chloride conversion, polymer formation, and lack of selectivity for the desired product.

More recently, several patents issued to Dynamit Nobel teach a gas phase, catalyzed reaction of vinylidene chloride and hydrogen fluoride. The only major product reported is 1,1,1-trifluoroethane in 98.8% to 99.8% yield, with very little or no 1,1-dichloro-1-fluoroethane produced. The reactions of vinylidene chloride and hydrogen fluoride disclosed by the aforesaid Dynamit Nobel patents are summarized in Table 1:

TABLE 1

| PAT. NO. | CATALYST | REACTION CONDITIONS | | PRODUCTS DISTRIBUTION (vol. %) | | | |
| --- | --- | --- | --- | --- | --- | --- | --- |
| | | TEMP. (°C.) | RATIO HF:$Cl_2C=CH_2$ | $CCl_2FCH_3$ | $CClF_2CH_3$ | $CF_3CH_3$ | $Cl_2C=Cl$ |
| U.S. Pat. No. 3,904,701 | $Bi(NO_3)_3$ over $Al_2O_3$ | 180 | 3.2 | 0 | 0.2 | 99.7 | 0.1 |
| | $Bi(NO_3)_3$ over $Al_2O_3$ | 205–220 | 3.7 | 0 | 0.2 | 99.8 | 0.1 |
| | $Bi(No_3)_3$ over $Al_2O_3$ | 210–225 | 3.3 | 0 | 0.4 | 98.9 | 0.7 |
| | $Bi(No_3)_3$ over $Al_2O_3$ | 215–225 | 3.4 | 0 | 0.2 | 99.6 | 0.2 |
| U.S. Pat. No. 3,803,241 | $CrCl_3/Al_2O_3$ | 150 | 3.5 (molar) | 0.2 | 0.2 | 99.8 | 0.8 |
| British Pat. No. 1,309,361 | $Mn(NO_3)_2$, $Bi(NO_3)_3$ over $Al_2O_3$ | 180 180 | 3.3 (volume) 3.3 (volume) | 0 0 | 0.3 0.2 | 99.6 99.7 | 0.1 0.1 |

In 1947, McBee et al. reported the liquid phase reaction of hydrogen fluoride and vinylidene chloride in a molar ratio of from 6.6:1 to 5.4:1, in an autoclave at between 140° C. and 210° C. under 5,000–6,000 psi pressure, using diphenylamine as a polymerization inhibitor. McBee et al., Ind. Eng. Chem. 39, 409–12 (1947). The authors reported in Table II yields of fluorinated product up to 90%. At a temperature of 140° C. the yield of fluorinated product was 76%. No 1,1-dichloro-1-fluoroethane was isolated. U.S. Pat. No. 2,637,747 discloses a similar process.

More recently, a liquid phase process for making 1-chloro-1,1-difluoroethane was disclosed in British Patent 1,556,131. A mixture of vinylidene chloride and hydrogen fluoride was heated in the presence of catalytic amounts of $SnCl_4$ in an autoclave at 60° C. to form 1,1-dichloro-1-fluoroethane (64.8%), 1-chloro-1,1-difluoroethane (26.7%), 1,1,1-trifluoroethane (2.1%), 1,1,1-trichloroethane (0.8%), oligomer (1.4%), and 4.2% unreacted vinylidene chloride. However, liquid phase reactions, which are generally conducted in batch rather than continuous fashion, are less desirable for economic reasons. Gas phase reactions are generally favored, as they are more readily adapted for continuous operation, and hence achieve maximum utilization of catalysts.

The various prior art processes involving hydrofluorination of vinylidene chloride have relatively low selectivity for 1,1-dichloro-1-fluoroethane. Clearly what is needed is a process capable of efficient gas phase conversion of vinylidene chloride with high selectivity for 1,1-dichloro-1-fluoroethane.

SUMMARY OF THE INVENTION

A process for selectively producing 1,1-dichloro-1-fluoroethane is provided. Hydrogen fluoride and vinylidene chloride are reacted in the vapor phase, in the presence of a catalyst, to form 1,1-dichloro-1-fluoroethane.

In another aspect, the invention is directed to a process for producing 1,1-dichloro-1-fluoroethane, 1-chloro-1,1-difluoroethane, or mixture thereof, by reacting hydrogen fluoride and vinylidene chloride in the vapor phase, in the presence of a catalyst to form a product comprising greater than 50 mole % 1,1-dichloro-1-fluoroethane, 1-chloro-1,1-difluoroethane, or mixture thereof.

As used herein, the expression "selectively produce" or "selectively producing" in reference to a designated product means that the product comprises greater than 50 mole % of the reaction product. The selectively produced product may hereinafter also be referred to as the "dominant product".

DETAILED DESCRIPTION OF THE INVENTION

The process of the invention may be utilized in either batch or continuous fashion. Generally, hydrogen fluoride and vinylidene chloride are contacted in the vapor phase at a molar ratio of from about 1:1 to about 10:1, preferably from about 1:1 to about 4:1, most preferably from about 1:1 to about 3:1. The process is characterized by a high level conversion of vinylidene chloride to product (up to 98 mole %), with a very high selectivity for 1,1-dichloro-1-fluoroethane. According to the process, the reaction product comprises generally at least 50 mole % of 1,1-dichloro-1-fluoroethane. Reaction selectivities for 1,1-dichloro-1-fluoroethane of 90 mole %, 98 mole %, and more, may be achieved with the present process. Moreover, few volatile by-products, substantially no tar, and substantially no oligomeric material are formed in the practice of the invention.

The process may be operated at any temperature favoring the conversion of vinylidene chloride to 1,1-dichloro-1-fluoroethane. Generally, the process is operated between from about room temperature (22° C.) to about 300° C., preferably from about 22° C. to about 200° C., most preferably from about 22° C. to about 100° C. The residence time of the reaction mixture at the reaction temperature may be selected in accordance with the desired extent of conversion of vinylidene chloride to product. Typically, the reactants are contacted for a period of time from about 1 second to about 150 seconds, preferably from about 10 seconds to about 150 seconds, most preferably from about 20 seconds to about 100 seconds.

Most preferably, the molar ratio of HF to vinylidene chloride ranges from about 1:1 to about 3:1, and the temperature ranges from about room temperature (22° C.) to about 100° C.

The reaction is generally carried out at atmospheric pressure, in the presence of a suitable catalyst. The catalyst may comprise, for example, aluminum fluoride, such as in the form of fluorided $\gamma$-aluminum oxide. Other suitable catalysts for use in the process include, by way of example and not by limitation, salts, preferably the chlorides, of the following species: bismuth (III), tin (IV), antimony (V) and arsenic (III). The chlorides are converted to the corresponding fluorides upon activation with hydrogen fluoride. Also useful are boron trifluoride, $KBF_4$, $HBF_4$, $B_2O_3$, $B(OH)_3$, and the like. The catalyst may be used directly, or may be carried on an appropriate catalyst support, such as activated carbon or $\gamma$-aluminum oxide. Such supported catalysts may be employed, for example, in the form of pellets or granules.

Boron trifluoride on $\gamma$-aluminum oxide is a particularly useful catalyst in the practice of the invention.

Tin(IV) salts, preferably $SnCl_4$, are also particularly useful. Upon hydrogen fluoride activation of activated carbon-supported $SnCl_4$, the resulting solid $SnF_4$ catalyst remains strongly adhered to the carbon support, without leaching from the catalyst bed. The catalyst remains active over the course of several days of continuous process operation.

I have found that by selecting the appropriate reaction conditions, either 1,1-dichloro-1-fluoroethane or 1-chloro-1,1-difluoroethane may be preferentially provided. For example, using a $SnCl_4$ on activated carbon catalyst, selectivity for 1,1-dichloro-1-fluoroethane is obtained at lower reaction temperatures, e.g. 30° C., and at lower molar ratios of hydrogen fluoride to vinylidene chloride, e.g. 1:1. Selectivity for 1-chloro-1,1-difluoroethane is obtained at higher reaction temperatures, e.g. 70° C., and at slightly higher reactant feed ratios, e.g. 2:1. Accordingly, the process of the invention may be conveniently adapted to produce either 1,1-dichloro-1-fluoroethane or 1-chloro-1,1-difluoroethane, selectively, with high conversion (97% and greater) of vinylidene chloride. The process of the invention may therefore be utilized to provide a product comprising greater than 50 mole % 1,1-dichloro-1-fluoroethane, 1-chloro-1,1-difluoroethane, or mixture thereof.

The process may be operated with or without a carrier gas. If a carrier gas is utilized, the preferred gas for this purpose is nitrogen, in the amount of 0–20 volume percent based upon the total volume of the reactants. Other suitable carrier gases are known to those skilled in the art.

The instant process may be carried out in a batch, semi-continuous, continuous or cyclic type process. Preferably, the process is conducted in continuous fashion, comprising continuously feeding gaseous hydrogen fluoride and gaseous vinylidene chloride into a reactor in the presence of a catalyst, and continuously withdrawing 1,1-dichloro-1-fluoroethane from the reactor. In a typical continuous operation, hydrogen fluoride and vinylidene chloride are passed through a tubular reactor loaded with hydrogen fluoride-activated catalyst. The reaction product, being predominantly 1,1-dichloro-1-fluoroethane, is removed from the reactor bottom and passed to a suitable scrubbing tower for removal of HF by the action of a countercurrent alkaline stream. The alkaline stream may comprise, for example, 1–5N aqueous potassium hydroxide. Other aqueous hydroxides such as sodium hydroxide or calcium hydroxide may be advantageously utilized. The scrubbed product, substantially free of HF is then passed to a drying tower, packed with a suitable drying agent, e.g., anhydrous calcium sulfate.

The materials of construction of the reactor for use in the present process are not critical, except that they should possess the necessary structural and physical characteristics to withstand the reaction conditions.

The present invention is illustrated in more detail by reference to the following non-limiting examples.

EXAMPLE 1

Harshaw pelletized aluminum oxide (50 grams) was loaded into a 1 inch (inside diameter)×13 inch tubular reactor (Hastelloy C). The catalyst was activated for 15 hours at 650° C., using air fed to the reactor at the rate of 20 cm³/minute through a valve located at the reactor top. Air activation was followed by hydrogen fluoride activation at 550° C. utilizing hydrogen fluoride fed at a rate of 0.2 g/minute and nitrogen fed at a rate of 20 cm³/minute. A total of 60 grams of hydrogen fluoride were fed into the reactor over 5 hours during the catalyst activation process. A mixture of hydrogen fluoride and vinylidene chloride in an 8:1 molar ratio was then fed into the reactor. The vinylidene chloride feed contained 6% oxygen and 25% nitrogen, based upon the volume of the vinylidene chloride feed. The reactor was maintained at 150° C. The reaction products were withdrawn from the bottom of the reactor after a 20 second contact time. Hydrogen fluoride was removed by passing the products through a scrubbing tower containing a continuously circulating countercurrent solution of 1-5N aqueous potassium hydroxide. The scrubbed organic products were then passed through a drying tower packed with anhydrous calcium sulfate. The conversion of reactant to product was periodically checked by diverting product from the drying tower to a gas chromatograph equipped with an electronic integrator. The mass balance was evaluated by passing the outlet gas from the gas chromatograph through a wet test meter. Gas chromatography analysis indicated a steady 23 mole % conversion of vinylidene chloride to product, with 100% selectivity for 1,1-dichloro-1-fluoroethane.

EXAMPLE 2

The same apparatus and procedure were used as described in Example 1, except that the reaction temperature was increased to 175° C. Conversion of vinylidene chloride was observed to increase to 50 mole %, with a selectivity for 1,1-dichloro-1-fluoroethane of 99.4%.

EXAMPLE 3

The same apparatus and procedure were used as described for Example 1 except that the contact time of the reactants in the reactor was increased to 43 seconds, the nitrogen feed was eliminated, the oxygen feed was increased to 17% based upon the volume of the vinylidene chloride feed, and the reaction temperature was increased to 175° C. Under these conditions, the conversion of vinylidene chloride was observed to increase to 65 mole %, with a selectivity for 1,1-dichloro-1-fluoroethane of 100%.

EXAMPLE 4

Fifty grams of fluorided γ-aluminum oxide was loaded into a 1 inch (inside diameter)×13 inch tubular reactor (Hastelloy C) and heated to 50° C. A mixture of vinylidene chloride (0.07 g) and hydrogen fluoride (0.04 g), in a 3:1 mole ratio were fed from the top of the reactor together with 0.6 cm$^3$ boron trifluoride (1.4 molar % of the hydrogen fluoride feed). The reaction products were withdrawn from the reactor after the reactants were in contact for 25 seconds. After scrubbing hydrogen fluoride from the product stream and drying the organic product as described in Example 1, analysis of the product by gas chromatography as in Example 1 indicated 98 mole % conversion of vinylidene chloride, with 98 mole % selectivity for 1,1-dichloro-1-fluoroethane, and 2% selectivity for 1-chloro-1,1-difluoroethane.

EXAMPLE 5

Thirty grams of pelletized γ-alumina loaded into a 1 inch (inside diameter)×13 inch tubular reactor (Hastelloy C) was activated with air at 650° C. for 18 hours, followed by hydrogen fluoride activation at 550° C. utilizing a hydrogen fluoride feed of 0.1 gram per minute for 6 hours and a N$_2$ feed of 20 cm$^3$/minute. Boron trifluoride (1.2 gram) was fed into the reactor with excess hydrogen fluoride to form HBF$_4$. A mixture of hydrogen fluoride and vinylidene chloride was then fed into the reactor as in Example 1 in a 3:1 molar ratio. The reaction products were withdrawn from the reactor after the reactants were in contact for 30 seconds. The product stream was scrubbed and dried as in Example 1. 98 mole % conversion of vinylidene chloride to product was observed, with a 1,1-dichloro-1-fluoroethane selectivity of 99 mole %.

The practice of the invention is further illustrated in the following examples, utilizing a tin(IV) chloride on activated carbon catalyst. The data from certain of these examples is listed in Table 2.

EXAMPLE 6

One hundred grams of activated carbon (Calgon CPG) was placed in a 250 ml round bottom flask interconnected to a gas inlet line and a vacuum line, and evacuated for 3 hours at 100° C. Nitrogen gas was introduced into the flask at 100° C., followed by the addition of SnCl$_4$ (101.6 g, 39 mol, 1 ml/min) at 100° C. using a syringe pump, in such a way that the liquid SnCl$_4$ dripped along the wall of the flask. The SnCl$_4$ was absorbed readily by the activated carbon to form a dried SnCl$_4$ on activated carbon catalyst containing 0.0017 mole SnCl$_4$ per gram of catalyst. The catalyst (74.9 g) was loaded into the reactor described in Example 1 and heated to 50° C. with N$_2$ being added at the rate of 5 cm$^3$/min for 18 hours. Hydrogen fluoride gas and N$_2$ were fed over the catalyst at the rate of 0.1 g/min and 5 cm$^3$/min, respectively, for 2 hours. After the catalyst was completely activated, gaseous hydrogen fluoride and gaseous vinylidene chloride were fed together into the reactor in a molar ratio of 2:1 (0.03 g/min HF; 0.07 g/min vinylidene chloride) with 5 cm$^3$/min N$_2$. The reactant contact time was 82 seconds. Under these conditions, conversion of vinylidene chloride was 99.8 mole % with 68.6 mole % selectivity for 1,1-dichloro-1-fluoroethane. Additional products included 1-chloro-1,1-difluoroethane (29.5%), 1,1,1-trifluoroethane (0.9%) and 1,1,1-trichloroethane (1%). Reactor performance stayed substantially constant over the course of several days.

EXAMPLE 7

The same apparatus and procedure were used as described in Example 6, except that the molar feed ratio of hydrogen fluoride to vinylidene chloride was decreased from 2:1 to 1.1:1. Conversion of vinylidene chloride dropped slightly to 98 mole %. Selectivity for 1,1-dichloro-1-fluoroethane increased to 93 mole %. Selectivity for the other reaction products was as follows: 1-chloro-1,1-difluoroethane (5.8%), 1,1,1-trifluoroethane (0.25%) and 1,1,1-trichloroethane (0.91%).

EXAMPLE 8

The same apparatus and procedure were used as described in Example 7, except that the reactor temperature was decreased from 50° C. to 30° C. The reactant contact time was 82 seconds. Conversion of vinylidene chloride remained very high (97.6 mole %,), as did selectivity for 1,1-dichloro-1-fluoroethane (94.5 mole %,). Selectivity for 1-chloro-1,1-difluoroethane (5.4%) and 1,1,1-trifluoroethane (0.1%) remained essentially the same. The reactor performance at 0° C. at 1.1:1 molar ratio hydrogen fluoride to vinylidene chloride stayed constant for several days without any evidence of catalyst deactivation or deterioration.

EXAMPLES 9-11

A catalyst comprising 0.0027 moles of SnCl$_4$ per gram of catalyst was prepared as follows. To 100 grams of activated carbon (Calgon CPG) was slowly added 175.6 g (0.67 mol) of SnCl$_4$. The resulting catalyst (90.8 g) was placed in the reactor described in Example 1.

The catalyst was activated by heating to 50° C., with N₂ being added at the rate of 5 cm³/min for 18 hours, followed by hydrogen fluoride (0.1 g/min) activation at 50° C. together with 5 cm³/min N₂ for 5 hours. After the catalyst was completely activated, a mixture of hydrogen fluoride and vinylidene chloride gas in a 1:1 or 2:1 ratio at temperatures of 30, 50 and 75° C. were fed into the reactor as described in Example 6. The results are shown in Table 2.

vinylidene chloride. The product distribution, in mole percent, was as follows:

| | |
|---|---|
| 1,1-dichloro-1-fluoroethane | 25.8% |
| 1-chloro-1,1-difluoroethane | 70.2% |
| 1,1,1-trifluoroethane | 2.98% |
| 1,1,1-trichloroethane | 0.19% |
| trichloroethylene | 0.88% |

TABLE 2

| Example | T (°C.) | Molar Ratio HF:CH$_2$=CCl$_2$ | % N$_2$ | Contact Time (sec.) | Conversion CH$_2$=CCl$_2$ (mole %) | PRODUCT DISTRIBUTION (mole %) | | | | |
|---|---|---|---|---|---|---|---|---|---|---|
| | | | | | | CH$_3$CCl$_2$F | CH$_2$CClF$_2$ | CH$_3$CF$_3$ | CH$_3$CCl$_3$ | Cl$_2$C=CHCl |
| 6 | 50 | 2:1 | 7.2 | 74 | 99.8 | 68.8 | 29.5 | 0.9 | 0 | 0 |
| 7 | 50 | 1.1:1 | 7.0 | 64 | 98.0 | 93.0 | 5.8 | 0.25 | 0.91 | 0 |
| 8 | 30 | 1.1:1 | 31.8 | 82 | 97.6 | 94.5 | 5.4 | 0.1 | 1.0 | 0 |
| — | 75 | 2.5:1 | 7.5 | 73 | 99.7 | 50.2 | 47.4 | 1.4 | 0.4 | 0.6 |
| 9 | 30 | 1:1 | 41.3 | 78 | 98.1 | 93.3 | 5.4 | 0.1 | 0.9 | 0.3 |
| 10 | 50 | 2:1 | 9.3 | 72 | 99.9 | 60.7 | 37.8 | 1.0 | 0.3 | 0.2 |
| 11 | 75 | 1:1 | 9.5 | 68 | 99.8 | 45.1 | 52.3 | 1.9 | 0.4 | 0.3 |
| 12 | 30 | 2:1 | 8.1 | 58 | 99.8 | 83.4 | 15.5 | 0.4 | 0.6 | 0.2 |
| 13 | 50 | 2:1 | 7.4 | 66 | 98.7 | 73.4 | 24.6 | 1.3 | 0.4 | 0.3 |
| 14 | 75 | 2:1 | 7.6 | 63 | 98.2 | 13.4 | 74.8 | 10.8 | 0.2 | 0.8 |

EXAMPLES 12-14

In a similar manner, a catalyst comprising 0.0027 moles SnCl₄ per gram of catalyst was prepared using activated carbon (Calgon BPL). The catalyst was activated as before, and its performance evaluated at 30, 50 and 75° C. using a 2:1 molar feed ratio of hydrogen fluoride to vinylidene chloride. The results are summarized in Table 2.

Particularly high selectivity for 1,1-dichloro-1-fluoroethane was achieved with a tin (IV) chloride catalyst at 30° C. At this temperature, selectivities for 1,1-dichloro-1-fluoroethane of 93.1, 93.3 and 83.4 mole % resulted, from 1.1:1, 1:1 and 2:1 hydrogen fluoride to vinylidene chloride molar feed ratios, respectively. Moreover, the reaction is characterized by an extremely high vinylidene chloride conversion, being 97.6 mole % and greater.

Examples 15-18 illustrate the practice of the invention utilizing a 0.0017 mole/g SnCl₄ catalyst in the absence of a carrier gas.

EXAMPLE 15

Activated carbon (100 grams, Calgon CPG) placed in a 250 ml round bottomed flask, which was interconnected into a nitrogen gas inlet and vacuum line, was evacuated for three hours at 100° C. After cooling the flask to room temperature, nitrogen gas was admitted to the flask followed by the addition of 200 ml of methylene chloride. SnCl₄ (101.6 grams, 0.39 mole) was added to the stirred suspension of the activated carbon in methylene chloride solution at a feed rate of 1 ml/min. After complete addition (45 minutes), the reaction mixture was further stirred at room temperature for one hour. The methylene chloride solvent was driven off by distillation at atmospheric pressure, and the reaction mixture was further dried using a vacuum pump at 50° C. From the catalyst obtained, 40 grams were loaded into the reactor described in Example 1 with 5 cm³/min N₂ for 18 hours, followed by hydrogen fluoride (0.1 g/min) and nitrogen (5 cm³/min) for two hours. Feeding a mixture of HF (0.03 g/min) and vinylidene chloride (0.07 g/min) at 75° C., gave 99.7% conversion of

EXAMPLE 16

The same catalyst and reactor feed of Example 15 were employed, except that the reaction temperature was lowered to 50° C. A 99.74 mole % conversion of vinylidene chloride was observed. Selectivity for 1,1-dichloro-1-fluoroethane increased to 88.1 mole %. The product distribution, in mole percent, was as follows:

| | |
|---|---|
| 1,1-dichloro-1-fluoroethane | 88.1% |
| 1-chloro-1,1-difluoroethane | 10.23% |
| 1,1,1-trifluoroethane | 0.31% |
| 1,1,1-trichloroethane | 0.76% |
| trichloroethylene | 0.6% |

EXAMPLE 17

The same catalyst from Example 15 was employed. The reaction was run at 30° C. with a reactant feed of 0.07 g/min vinylidene chloride and 0.02 g/min HF. Conversion of vinylidene chloride remained very high, 99.85 mole %. The product distribution, in mole percent, was as follows:

| | |
|---|---|
| 1,1-dichloro-1-fluoroethane | 68.4% |
| 1-chloro-1,1-difluoroethane | 30.2% |
| 1,1,1-trifluoroethane | 0.44% |
| 1,1,1-trichloroethane | 0.21% |
| trichloroethylene | 0.3% |

The processes described in each of Examples 15, 16 and 17 was run continuously for eleven days without evidence of catalyst deactivation.

Examples 18-19 illustrate the practice of the invention utilizing a catalyst comprising 0.0017 mole % SbCl₅ per gram of catalyst.

EXAMPLE 18

Activated carbon (105 grams, Calgon CPG) placed in a 250 ml round bottomed flask, which was interconnected into a nitrogen gas inlet and a vacuum line, was evacuated for four hours at 100° C. After completing the evacuation, the vacuum line was disconnected and nitrogen gas was admitted to the flask at 100° C. Antimony (V) chloride (117 g, 0.39 mole) was gradually added to the heated activated carbon with continuous shaking of the flask in such a way that SbCl5 was dripping on the wall of the flask. The dried catalyst (69.3 grams) was activated with nitrogen at 50° C. for 18 hours, fed at a rate of 5 cm³/min, followed by HF activation with 1 g/min HF for four hours. The catalyst performance was evaluated at 50° C. in the hydrofluorination of vinylidene chloride in the same reactor used in Example 1, at a feed rate of 0.03 g/min HF, 0.07 g/m vinylidene chloride and 10 cm³/min of N2. The reaction was run continuously for two days. Fifty mole % conversion of vinylidene chloride was observed, with a selectivity for 1,1-dichloro-1-fluoroethane of 93.4 mole %. The product distribution in mole percent, was as follows:

| | |
|---|---|
| 1,1-dichloro-1-fluoroethane | 93.4% |
| 1-chloro-1,1-difluoroethane | 3.3% |
| 1,1,1-trifluoroethane | 0.1% |
| 1,1,1-trichloroethane | 2.7% |
| trichloroethylene | 0.5% |

EXAMPLE 19

The reaction of Example 18 was repeated except that the temperature was raised from 50° C. to 75° C. Conversion of vinylidene chloride increased to 63 mole %. The product distribution, in mole percent, was as follows:

| | |
|---|---|
| 1,1-dichloro-1-fluoroethane | 94.5% |
| 1-chloro-1,1-difluoroethane | 3.9% |
| 1,1,1-trifluoroethane | 0.8% |
| trichloroethylene | 0.8% |

EXAMPLE 20

The same apparatus and procedure were used as described in Example 6, except that the amount of catalyst was reduced to 19.5 grams, the molar feed ratio of hydrogen fluoride to vinylidene chloride was increased from 2:1 to 2.3:1, the reaction temperature was increased to 134° C., and the contact time was reduced to 6 seconds. Under these conditions, conversion of vinylidene chloride was 99.9%. 15 The product distribution in mole percent, was as follows:

| | |
|---|---|
| 1,1-dichloro-1-fluoroethane | 97.9% |
| 1-chloro-1,1-difluoroethane | 1.69% |
| 1,1,1-trifluoroethane | 0.26% |
| other | 0.15% |

The present invention may be embodied in other specific forms without departing from the spirit or essential attributes thereof and, accordingly, reference should be made to the appended claims, rather than to the foregoing specifications, as indicating the scope of the invention.

I claim:

1. A process for selectively producing 1,1-dichloro-1-fluoroethane comprising continuously feeding gaseous hydrogen fluoride and gaseous vinylidene chloride to a reactor containing a solid catalyst selected from the group consisting of tin (IV) salts and antimony (V) salts, at a molar ratio of hydrogen fluoride to vinylidene chloride of from about 1:1 to about 10:1, for a period of time from about 1 second to about 150 seconds, at a temperature of from about 22° C. to about 300° C.

2. A process according to claim 1 wherein hydrogen fluoride and vinylidene chloride in a molar ratio from about 1:1 to about 4:1 are contacted for a period of time from about 10 seconds to about 150 seconds, at a temperature from about 22° C. to about 200° C.

3. A process according to claim 2 wherein hydrogen fluoride and vinylidene chloride in a molar ratio of from about 1:1 to about 4:1 are contacted for a period of time from about 20 seconds to about 100 seconds at a temperature of from about 22° C. to about 100° C.

4. A process according to claim 1 wherein at least about 90 mole % of the product comprises 1,1-dichloro-1-fluoroethane.

5. A process according to claim 1 wherein the catalyst is a tin (IV) salt.

6. A process according to claim 5 wherein the catalyst is SnCl4.

7. A process according to claim 6 wherein the catalyst is SnCl4 on activated carbon.

8. A continuous process for selectively producing 1,1-dichloro-1-fluoroethane comprising continuously feeding gaseous hydrogen fluoride and gaseous vinylidene chloride to a reactor containing a solid catalyst selected from the group consisting of tin (IV) salts and antimony (V) salts, and continuously withdrawing 1,1-dichloro-1-fluoroethane from the reactor.

9. A process according to claim 8 wherein the catalyst comprises a tin (IV) salt.

10. A process according to claim 9 wherein the catalyst comprises SnCl4.

11. A process according to claim 8 wherein the hydrogen fluoride and vinylidene chloride are in contact for a period of time from about 1 second to about 150 seconds.

12. A process according to claim 11 wherein the hydrogen fluoride and vinylidene chloride are in contact for a period of time from about 10 seconds to about 150 seconds.

13. A process according to claim 12 wherein the hydrogen fluoride and vinylidene chloride are in contact for a period of time from about 20 seconds to about 100 seconds.

14. A process according to claim 8 wherein hydrogen fluoride and vinylidene chloride are reacted at a temperature of from about 22° C. to about 300° C.

15. A process according to claim 14 wherein hydrogen fluoride and vinylidene chloride are reacted at a temperature of from about 22° C. to about 200° C.

16. A process according to claim 15 wherein hydrogen fluoride and vinylidene chloride are reacted at a temperature of from about 22° C. to about 100° C.

17. A process according to claim 8 wherein the reaction product comprises at least about 90 mole % 1,1-dichloro-1-fluoroethane.

18. A process according to claim 17 wherein the reaction product comprises at least about 98 mole % 1,1-dichloro-1-fluoroethane.

19. A process according to claim 8 wherein the molar ratio of hydrogen fluoride to vinylidene chloride in the reactor is from about 1:1 to about 10:1.

20. A process according to claim 19 wherein the molar ratio of hydrogen fluoride to vinylidene chloride in the reactor is from about 1:1 to about 4:1.

21. A process according to claim 8 wherein the catalyst is supported on a catalyst support selected from the group consisting of γ-aluminum oxide and activated carbon.

22. A process according to claim 21 wherein the catalyst comprises $SnCl_4$ on activated carbon.

23. A process according to claim 9 wherein the catalyst comprises $SnF_4$.

24. A process according to claim 8 wherein the catalyst comprises $SnF_4$.

25. A process according to claim 8 wherein the catalyst is a tin (IV) salt.

26. A continuous process for producing 1,1-dichloro-1-fluoroethane, 1-chloro-1,1-difluoroethane, or mixture thereof, comprising continuously feeding gaseous hydrogen fluoride and gaseous vinylidene chloride to a reactor containing a solid catalyst selected from the group consisting of tin (IV) salts and antimony (V) salts, and continuously withdrawing from said reactor a product comprising greater than 50 mole % 1,1-dichloro-1-fluoroethane, 1-chloro-1,1-difluoroethane, or mixture thereof.

27. A process according to claim 26 wherein hydrogen fluoride and vinylidene chloride are reacted in a molar ratio of from about 1:1 to about 10:1.

28. A process according to claim 26 for selectively producing 1,1-dichloro-1-fluoroethane.

29. A process according to claim 26 for selectively producing 1-chloro-1,1-difluoroethane.

30. A process according to claim 26 wherein the hydrogen fluoride and vinylidene fluoride are in contact for a period of time from about 1 second to about 150 seconds.

31. A process according to claim 30 wherein the hydrogen fluoride and vinylidene fluoride are in contact for a period of time from about 10 seconds to about 150 seconds.

32. A process according to claim 31 wherein the hydrogen fluoride and vinylidene fluoride are in contact for a period of time from about 20 seconds to about 100 seconds.

33. A process according to claim 26 wherein the hydrogen fluoride and vinylidene fluoride are reacted at a temperature of from about 22° C. to about 300° C.

34. A process according to claim 33 wherein the hydrogen fluoride and vinylidene fluoride are reacted at a temperature of from about 22° C. to about 200° C.

35. A process according to claim 34 wherein the hydrogen fluoride and vinylidene fluoride are reacted at a temperature of from about 22° C. to about 100° C.

36. A process according to claim 26 wherein the catalyst comprises a tin (IV) salt.

37. A process according to claim 36 wherein the catalyst is supported on a catalyst support selected from the group consisting of γ-aluminum oxide and activated carbon.

38. A process according to claim 37 wherein the catalyst comprises $SnCl_4$ on activated carbon.

39. A process according to claim 36 wherein the catalyst comprises $SnF_4$.

* * * * *